United States Patent [19]

Lindner et al.

[11] 4,166,393
[45] Sep. 4, 1979

[54] PROCESS AND APPARATUS FOR AUTOMATIC, CONTINUOUS, DESTRUCTION-FREE CHECKING, ESPECIALLY OF STONEWARE PIPES

[75] Inventors: Hans A. Lindner; Hans-Jürgen Thoma, both of Rodental, Fed. Rep. of Germany

[73] Assignee: Cremer & Breuer Keramische Betriebe GmbH, Frechen, Fed. Rep. of Germany

[21] Appl. No.: 808,655

[22] Filed: Jun. 21, 1977

[30] Foreign Application Priority Data

Jun. 23, 1976 [DE] Fed. Rep. of Germany ....... 2628178

[51] Int. Cl.² ............................................. G01N 29/00
[52] U.S. Cl. ..................................................... 73/579
[58] Field of Search .................................. 73/579, 582

[56] References Cited

U.S. PATENT DOCUMENTS 1,543,124  6/1925  Ricker ................................ 73/579 X

FOREIGN PATENT DOCUMENTS 495780  11/1938  United Kingdom .................... 73/579
1011472 12/1965  United Kingdom .................... 73/579

*Primary Examiner*—Stephen A. Kreitman
*Attorney, Agent, or Firm*—Friedman, Goodman & Teitelbaum

[57] ABSTRACT

Process and apparatus for a non-destructive continuous automatic quality control system monitoring a stoneware pipe and like objects, where the pipe is excited with a vibration generator up to a resonance frequency vibration, this vibration being measured with a vibration receiver, thereupon being registered and compared with values of a calibration curve. During the excitation and measuring, the pipe is borne on two turn crosses coated with rubber. The resonance frequency vibration is measured at the maximum of at least one antinode of vibration. The pipe is transported by a conveyor belt having rollers. A photoelectric pipe scanning system measures the nominal diameter of the pipe for preadjusting the position of the vibration receiver.

17 Claims, 4 Drawing Figures

PROCESS AND APPARATUS FOR AUTOMATIC, CONTINUOUS, DESTRUCTION-FREE CHECKING, ESPECIALLY OF STONEWARE PIPES

BACKGROUND OF THE INVENTION

The present invention relates to a process and to an apparatus for automatic, continous, destruction-free checking of stoneware pipes and similar objects with resonance frequency vibrations.

There has already been made an endeavor to test stoneware pipes without destruction using resonance frequency vibration measurements with low-frequency mechanical waves. The pipe was positioned over a vibrator, where the frequency was generated by a sound generator internally located in the center or middle of the pipe and was transmitted laterally to the wall of the stoneware pipe. The pipe stood vertically with its spigot end on a foam rubber mat. The spigot end, as defined in Webster's unabridged New International Dictionary, is the male end of a section of pipe which enters the hub end of the next section. The frequency was picked up with a sound pickup device positioned on the oppositely situated internal wall of the pipe, likewise being within the middle of the pipe. The measured resonance frequencies were, among other things, brought into correlation with the crushing strength of a certain type of pipe. As is well known in the art, the correlation of the crushing strengths to the resonance frequency vibrations is dependent upon or influenced by many variable factors such as the production material, the degree of firing, the nominal width, the length, the body thickness, as well as the porosity and moisture content of the pipes, so that assured interrelations or calibrations thereof cannot be guaranteed.

The known process, however, was unable to establish itself for quality monitoring in the stoneware industry, especially because of the position of the pipe, the type of vibration stimulation, the positioning of the vibration measuring heads within the pipe, as well as the sensitivity of the apparatuses to any interference sound. Thus, a dependable allocation of the measured resonance frequency vibrations to a particular pipe type was not possible. Moreover, the known process is not suited for automation which provides a continuous quality monitoring because the handling and centering of the measuring instruments for coupling to the vertically standing pipes, especially in the testing of pipes of differing nominal diameters, require considerable application of machinery.

SUMMARY OF THE INVENTION

The purpose of the present invention is to provide a process as well as an apparatus which permit an automatic, continuous quality monitoring of stoneware pipes by a resonance frequency system, which is virtually independent of any interference noise, without resetting same for pipes of different nominal diameters, and which operates rapidly, where the process assures a dependable correlation between the crushing strength of the pipe and the resonance frequency of the system.

Accordingly, it is an object of the present invention to provide an improved process and apparatus for a non-destructive continuous automatic quality control system monitoring a stoneware pipe and like objects which solves the aforementioned problems of the prior art.

These problems are solved according to the present invention by a process for the destruction-free continuous quality monitoring of stoneware pipes and similarly formed objects, in which the pipe is excited by a vibration generator up to a resonance frequency vibration and this vibration is measured by at least one vibration receiver, and then is registered and compared with values of a calibration curve having a correlation of the resonance frequency vibration with the crushing strength of the pipe. This process is distinguished in that each pipe is borne during the excitation and measurement in at least one vibration node line and the resonance frequency vibration is excited and measured in the maximum of at least one vibration loop or antinode. In the case of the resonance, as is well known, there occur standing waves. In the vibration nodes, the mass particles are continuously at rest, and inbetween the nodes lie the vibration loops or antinodes. The vibration nodes and vibration loops or antinodes are also designated as minima and maxima, respectively.

The bearing of the pipe can take place on the outer shell of the pipe at one or more node lines. It is especially advantageous if the pipe or tube is moved into a horizontal position, set into vibration and then moved off. According to a special form of the present invention, the excitation and measurement of the resonance frequency vibration is carried out on a shell segment of the pipe, the excitation being carried out with a vibration generator and the measurement being made with two vibration receivers. Through this arrangement, it is possible to relate the measured resonance frequencies to a particular resonance frequency vibration, and thereby to evaluate the measurement result reproducibly. It has been proved that in the monitoring of stoneware pipes of a length of 1 to 2 meters, the measuring results turn out to be especially clear, where the vibration generator lies between the pipe spigot and the first node of the resonance frequency vibration, preferably in the region of 0.1 times the pipe length measured from the pipe spigot.

With the particular resonance vibration, the pipe can vibrate with four nodes transverse to the longitudinal axis of the pipe and two nodes in the longitudinal direction of the pipe. The optimal position of the vibration generator is in the region between the first vibration node (which determines the position of the first vibration receiver) and the second vibration node (which determines the position of the second vibration receiver), especially at about 0.3 times the pipe length measured from the pipe spigot. The optimal position of the second vibration receiver lies in the region nearest to the second vibration node measured from the pipe spigot.

In order, insofar as possible, to exclude the susceptibility to interference sound, it has been proved advantageous, for the excitation and measurement of the resonance frequencies, to use generators and receivers insenstive to interference noise, in particular, such as the use of magnetic systems which are well known and commercially available. For example, such magnetic systems or magnetic generators and receivers are manufactured by Ling Dynamic Systems Limited of Baldock Road, Royston, Hertfordshire, England, as their Ling Dynamic Systems 200 Series Vibrators for use in small scale vibration testing or as non-seismic pick-ups, being widely used by technical institutes, as set forth in their instruction manual having an original date of use of June 21, 1973.

According to a special form of the process of the present invention, the pipe is borne on at least two lower node lines, preferably on four lines of the lower node lines, and is excited between and underneath these lines with the resonance frequency vibration, where the vibrations are measured on the excitation shell segment. In this case, the pipe is preferably borne on two turnable crosses coated with rubber or rubber-like material. The crosses are arranged at a spacing from one another that corresponds to between 0.6 to 0.8 times the length of the pipe, preferably 0.7 times the length. Further, essential features of the process of the invention are set forth hereinafter below.

The object of the present invention is, further, an apparatus for the automatic continuous execution of the process of this invention, which includes essentially a bearing for the pipes, vibrator and vibration-receiver elements, as well as registering installations, and which is distinguished in that it has a transport band or conveyor with transport rollers, a photoelectric pipe scanning system, two rotary crosses with rubber coatings thereon, two vibration receivers, as well as a vibration generator. Further features essential to the present invention of the apparatus are set forth hereinafter below.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawings like reference characters designate like parts.

DESCRIPTION OF THE PREFERRED EMBODIMENT

Figure 1:
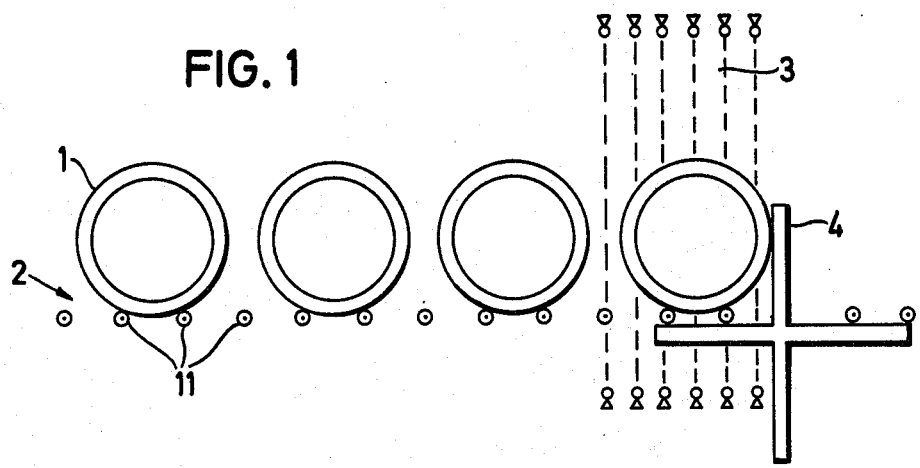
FIG. 1 shows a schematic representation of the control apparatus of the present invention.
Figure 3:
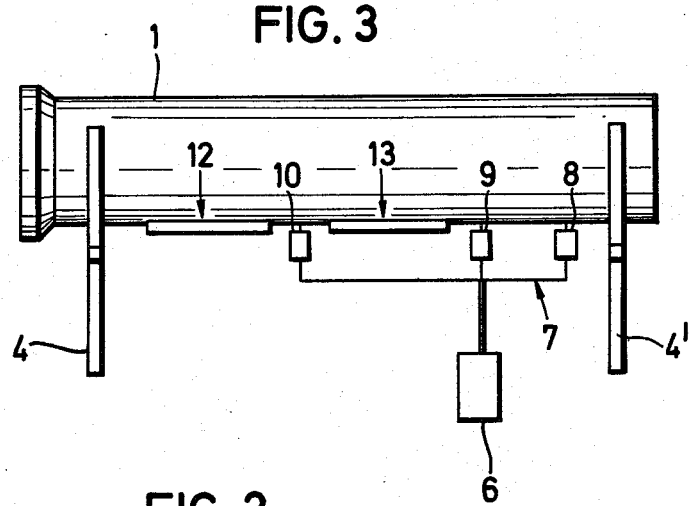
FIG. 3 is a side view of the control apparatus.

The apparatus for the execution of the process of the present invention, as shown in the drawings, includes a conveyor belt 2, which is composed preferably of transport rollers 11. The spacing of the transport rollers 11 from one another is chosen in such a way that the horizontally conveyed pipe 1 with the smallest nominal diameter can still be conveyed without appreciable sagging, this spacing being substantially less than the smallest nominal diameter, as shown in FIG. 1. The transport rollers are preferably arranged in two rows 12, 13, as shown in FIG. 3, in order to provide space for the measuring apparatuses and the bearing elements for the pipe 1 to be tested, as set forth below.

The apparatus of the present invention has, further, two turn crosses 4 and 4', which are preferably constructed with right angle sections and whose axes of rotation are arranged underneath or below the path of the conveyor belt and transversely thereto. As shown, turn cross 4' is adjacent to the pipe spigot. The turn crosses 4, 4' are provided with a rubber or rubber-like material coating in order to exclude interfering vibrations. Laterally underneath the conveyor belt 2 between the turn crosses 4, 4', there is provided a measuring system 7 with a conventional vibration generator 9 and two conventional vibration receivers 8, 10. The individual elements of the measuring system 7 are located preferably in the same horizontal plane as shown in FIG. 3, and are mechanically coupled with one another by suitable conventional members well known in the art. The measuring system 7 is elevationally adjustable by a conventional lift device 6 on which it is mounted. Moreover, the apparatus according to the present invention has a photoelectric pipe scanning system 3.

For the continuous automatic testing, the stoneware pipes 1 lying on the conveyor belt 2 are fed to the measuring system 7. Before each pipe 1 reaches the turn cross bearing 4, 4' there takes place a nominal diameter measurement of the pipe with the photoelectric devices 3, known per se in the art. The measurement result of the photoelectric pipe scanning serves the purpose of preadjusting the electronic portion of the automatic frequency measuring system and the related mechanical system, especially for determining the position of the vibration receivers 8, 10 and the generator 9 by raising or lowering the lift device 6 accordingly. Here the nominal diameter-dependent frequency range is preselected, as well as the frequency range and phase displacement between the vibration generator 9 and vibration receivers 8, 10. It is then possible to carry out the automatic measurement. If the resonance frequency of the pipe to be tested lies in the preselected range, as indicated on the above mentioned calibration curve, then it is a faultless pipe and is correspondingly conducted or conveyed onward in the system. In the contrary case where the resonance frequency is not in the preselected range and the pipe is thus faulty, the pipe is sorted out of the system through conventional transport devices coupled with the measuring device. It is noted, that the above mentioned calibration curve, which correlates the resonance frequency vibration with the crushing strength of the pipe, can be obtained by one skilled in the art by using known procedures, where the normal process of obtaining the calibration curve does not form a part of the present invention.

With the measurement of the nominal diameter, there are simultaneously initiated, the following: stopping of the belt 2; turning of the crosses 4, 4' through 45°; coupling in of the measuring installation 7 over the lift device 6; switching on and switching off of the measuring devices 8, 9, 10; turning the turn crosses 4, 4' through a further 45°; and setting the conveyor belt in operation.

Figure 2:
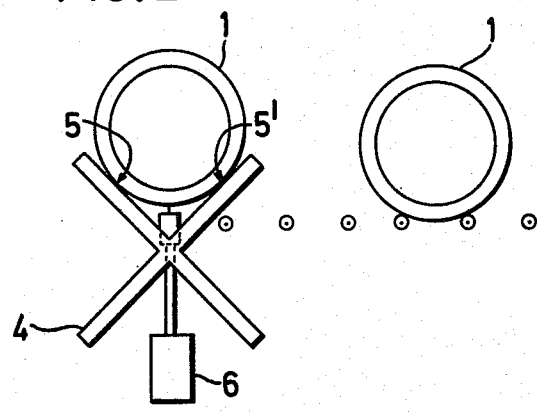
FIG. 2 shows a part of the control apparatus in a measuring position.

As FIG. 2 shows, the pipe 1 is borne or mounted at the two node lines 5, 5' on the turn cross 4, which is constructed with its members perpendicular to each other to provide four right angle sections, where each section in turn receives a pipe. This form of construction makes the bearing of the pipes independent of each nominal diameter, since for the resonance frequency in the excitation, according to the present invention, the node lines are always offset by 45° on both sides of the excitation, where the arms of each cross 4, 4' contact each pipe tangentially regardless of the nominal diameter of these lines. It is also possible to choose other angles than right angles of the turn crosses, if other resonance frequencies are to be measured. It is important that the coupling of vibration generator and vibration receivers to the pipe 1 take place vertically perpendicularly above each turn cross axis of the turn crosses 4, 4' to obtain the above mentioned equal offset angles of 45°.

With knowledge of the present invention, the spacing of the turn crosses from one another can be made variably, preferably automatically, and by one skilled in the art, where the selected spacing setting-in thereof can be coupled with the frequency range pulse generation. This makes it possible to obtain the most favorable bearing position of the turn crosses with respect to the particular pipe length. Likewise, it is possible for one skilled in the art also to make the spacing of the vibration receivers to the vibration generator variable, preferably automatically, where this spacing would depend upon and correspond to the pipe length, so that the optimal coupling position thereof for a particular type of pipe being tested can be set-in into the system.

Preferably, the vibration generator 9 is arranged in the region between the node lines at the turn cross 4' and the second node lines at the turn cross 4 as shown in FIG. 3, being at about 0.3 times the pipe length measured from the pipe spigot. The vibration receiver 10 is arranged in the region nearest the second node lines and the vibration receiver 8 is in the region nearest the first node lines. The distance between the generator 9 and the receiver 10 is 1.1 to 1.4 times the distance between the generator 9 and the receiver 8, preferably being about 1.3. This makes possible, in particular, the control or relationship of the measured resonance frequency vibrations to the particular pipe vibration type, which is of essential importance for the determinative value of the test.

The insensitivity to noise of the process and of the apparatus of the present invention, respectively, is achieved through the use of conventional high-power magnetic vibration generators and receivers, which are well known to those skilled in the art, as well as through the geometrically defined vibration coupling. Even strong hammer blows during the frequency measuring do not affect the result. The clear relationship of the measured pipe resonance frequencies to the pipe vibration type is likewise assured through the geometrically defined vibration coupling relative to the vibration nodes transverse to the longitudinal axis of the pipe and the vibration nodes in the longitudinal direction of the pipe in respect to the chosen pipe vibration type.

With the automatically operating apparatus according to the present invention, a destruction-free quality appraisal is possible in the continuous production thereof. The distribution of the measured resonance frequencies, keyed according to the characteristics of the pipes, permits a faultless indication of the uniformity and the general quality of the production. The process of the present invention makes it possible to separate-out pipes with low resonance frequencies caused, for example, by increased porosity or cracks which occur principally in the region of the pipe spigots, and accordingly, in conformity with the correlation between the resonance frequency and the crushing strength, to separate-out pipes with low crushing strengths, and thereby to bar complaints from the users which can be costly to the manufacturer. Through the automatic manner of operation of the apparatus of the present invention, there is obtained a substantial saving in costs in the operation itself with a near hundred percent control, because in particular, the extremely time-consuming prior art crushing strength testing which is based on the destruction of faultless pipes can be avoided. Moreover, the testing process of the present invention obtains a high indicative value in regard to the freedom from faults of the stoneware pipes delivered, and therefore offers a high security against damages in use.

Figure 4:
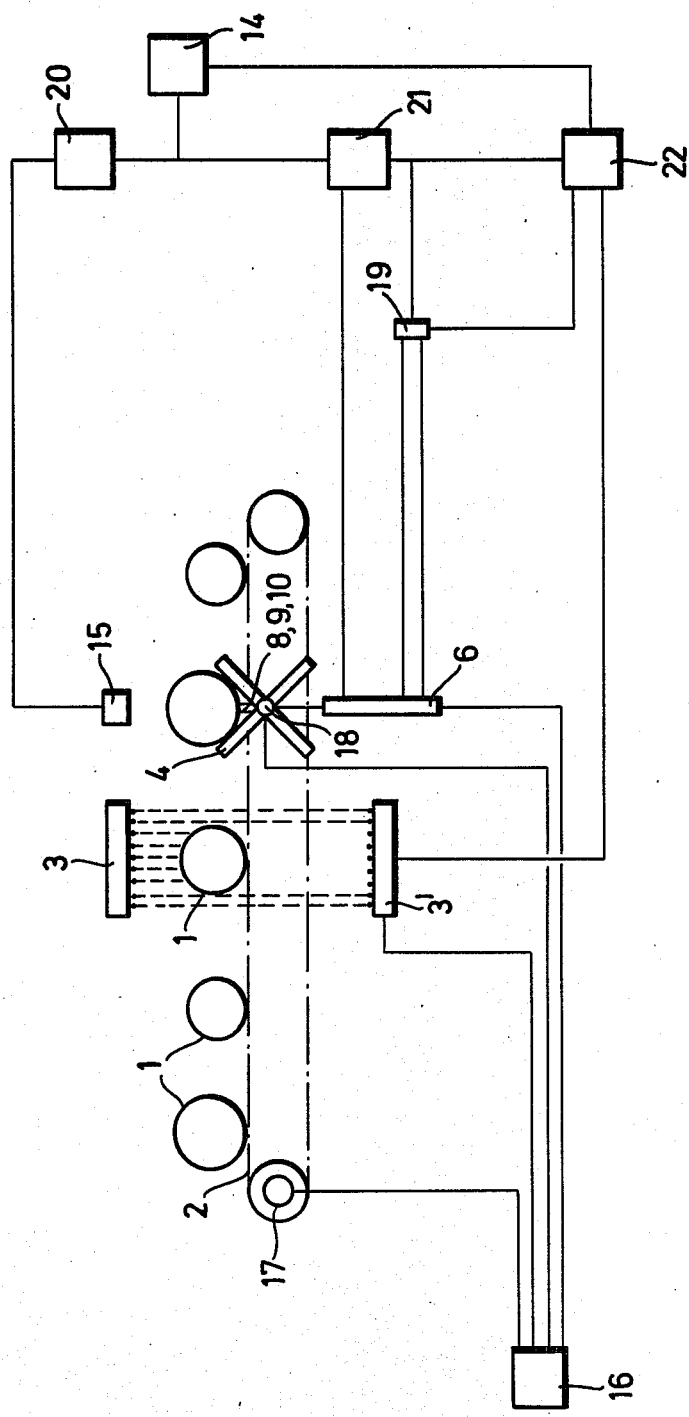
FIG. 4 shows a schematic representation of the automation circuit of the present invention.

FIG. 4 represents an apparatus according to the present invention, showing a schematic circuit diagram of electrical arrangements. These electrical arrangements include a conventional main control unit 16 for the entire measuring course, the transmitter 3 and the receiver 3' of the photoelectric pipe nominal diameter scanning system, a conventional measuring head selector 19, a conventional starting frequency generator 22, a conventional resonance frequency measuring apparatus 21 with an automatic resonance frequency finder, a conventional classifying device 20 for various resonance frequency ranges and a conventional measurement value printer 14. These elements control, according to corresponding suitable and conventional switching devices, a conventional drive motor 17 of the conveyor belt 2, a conventional turn cross drive 18, the resonance frequency measuring head lift device 6, and a conventional color marking device 15, which marks the tested pipe according to quality class. With the photoelectric pipe nominal diameter scanning system 3 and 3', there is automatically selected, among other things mentioned above such as the starting and stopping of the conveyor belt, the resonance frequency range by the starting frequency generator 22, which is dependent upon the nominal diameter of each pipe in turn being tested.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A process for a non-destructive continuous automatic quality control system of monitoring a stoneware pipe and like objects, said process comprising:
   positioning the pipe for support on at least one vibration node;
   exciting the positioned pipe with a vibration generator to obtain a resonance frequency vibration of the pipe;
   measuring the resonance frequency vibration simultaneously on at least two points of a vibrating segment of the pipe with two spaced apart vibration receivers;
   registering a value of the resonance frequency vibration obtained from the two vibration receivers; and
   comparing the registered value with predetermined values of a calibration curve having a correlation of resonance frequency vibration with crushing strength of the pipe to determine the crushing strength and structural faults of the pipe.

2. A process according to claim 1, wherein said exciting produces four nodes transverse to a longitudinal axis of the pipe and two nodes in a longitudinal direction of the pipe.

3. A process according to claim 2, wherein the supporting of the pipe is on at least two of said four transverse nodes, and said exciting of said vibration generator is applied on said vibrating segment between said two transverse nodes.

4. A process according to claim 1, wherein said positioning includes disposing the pipe in a horizontal position, and conveying the pipe away after said measuring.

5. A process according to claim 1, wherein said exciting includes providing a vibration between a spigot end of the pipe and the one vibration node at approximately 0.1 times length of the pipe as measured from the spigot end.

6. A process according to claim 1, wherein said exciting includes providing a vibration between first and second vibration node lines at approximately 0.3 times the length of the pipe as measured from a spigot end of the pipe.

7. A process according to claim 1, wherein said exciting is provided by a magnetic vibration generator and said measuring is by two magnetic vibration receivers.

8. A process according to claim 1, wherein said positioning includes disposing the pipe in a horizontal position on two rotatable turn crosses which are coated with rubber.

9. A process according to claim 8, wherein said positioning includes spacing the two turn crosses apart at a distance from each other of from 0.6 to 0.8 times length of the pipe.

10. An apparatus for a non-destructive continuous automatic quality control system of monitoring a stoneware pipe and like objects, said apparatus comprising:
 positioning means for supporting the pipe in a horizontal position on at least one vibration node;
 exciting means for vibrating the pipe to obtain a resonance frequency vibration of the pipe in the horizontal position, said exciting means including a vibration generator;
 measuring means for measuring the resonance frequency simultaneously on at least two points of a vibrating segment of the pipe, said measuring means including two spaced apart vibration receivers; and
 registering means for recording a value of the resonance frequency vibration obtained from said two vibration receivers, so that the recorded value can be compared with predetermined values of a calibration curve having a correlation of resonance frequency vibration with crushing strength of the pipe to determine the crushing strength and structural faults of the pipe.

11. An apparatus according to claim 10, wherein said vibration receivers and generator are mechanically coupled in a common horizontal plane, lifting means for vertically adjusting said vibration receivers and generator to a preselected horizontal position, and photoelectric pipe scanning system means associated with said lifting means to obtain nominal diameter of the pipe for determining said preselected horizontal position.

12. An apparatus for a non-destructive continuous automatic quality control system of monitoring a stone pipe and like objects, said apparatus comprising:
 positioning means for supporting the pipe in a horizontal position, said positioning means including two spaced apart turn crosses having a rubber coating to receive and hold the pipe during excitation thereof;
 exciting means for vibrating the pipe to obtain a resonance frequency vibration of the pipe when supported in the horizontal position on said two turn crosses; said exciting means including a vibration generator;
 measuring means for measuring the resonance frequency, said measuring means including at least one vibration receiver; and
 registering means for recording a value of the resonance frequency vibration obtained from said at least one vibration receiver, so that the recorded value can be compared with predetermined values of a calibration curve having a correlation of resonance frequency vibration with crushing strength of the pipe to determine the crushing strength and structural faults of the pipe.

13. An apparatus according to claim 12, further including a conveyor belt having transport rollers to transport the pipe to said two turn crosses.

14. An apparatus according to claim 13, wherein said conveyor belt includes two parallel running series of said transport rollers.

15. An apparatus according to claim 14, wherein said vibration receiver is disposed between said two parallel running series of said transport rollers.

16. An apparatus according to claim 12, wherein said measuring means includes two vibration receivers, said two vibration receivers and vibration generator are disposed between said two turn crosses and vertically perpendicularly above common axes of rotation of said turn crosses.

17. An apparatus according to claim 16, wherein said vibration generator is disposed horizontally between said vibration receivers.

* * * * *